United States Patent [19]

Millar

[11] Patent Number: 4,850,358
[45] Date of Patent: Jul. 25, 1989

[54] METHOD AND ASSEMBLY FOR INTRODUCING MULTIPLE DEVICES INTO A BIOLOGICAL VESSEL

[75] Inventor: Huntly D. Millar, Houston, Tex.

[73] Assignee: Millar Instruments, Inc., Houston, Tex.

[21] Appl. No.: 119,616

[22] Filed: Nov. 12, 1987

Related U.S. Application Data

[63] Continuation-in-part of Ser. No. 931,273, Nov. 14, 1986, Pat. No. 4,771,782.

[51] Int. Cl.[4] ............................................. A61B 5/00
[52] U.S. Cl. .................................... 128/637; 128/673; 128/675; 128/748
[58] Field of Search ............... 128/637, 642, 672, 673, 128/674, 675, 748, 772

[56] References Cited

U.S. PATENT DOCUMENTS

| | | |
|---|---|---|
| 1,747,407 | 2/1930 | Wappler . |
| 3,038,465 | 6/1962 | Allard et al. .......................... 128/715 |
| 3,853,130 | 12/1974 | Sheridan . |
| 3,995,623 | 12/1976 | Blake et al. . |
| 4,456,013 | 6/1984 | De Rossi et al. .................... 128/675 |
| 4,613,323 | 9/1986 | Norton et al. . |

FOREIGN PATENT DOCUMENTS

| | | |
|---|---|---|
| 0180348 | 5/1986 | European Pat. Off. . |
| 2006019 | 5/1979 | United Kingdom . |
| 2127294 | 4/1984 | United Kingdom . |

OTHER PUBLICATIONS

Schneider Medintag Brochure "Monorail-Bonzel Coronary Dilation System".

Primary Examiner—Max Hindenburg
Assistant Examiner—Randy Citrin
Attorney, Agent, or Firm—Arnold, White & Durkee

[57] ABSTRACT

A method and assembly for inserting a plurality of sensors into a biological fluid vessel for diagnosing the condition of the vessel or fluid. A pressure sensor is described which is particularly adapted for use with a steerable guidewire for selective positioning in the vessel. In one application, the method is used in coronary diagnosis, to determine the pressure gradient across a coronary valve or stenosis in the coronary arterial tree. In this method, a guiding catheter is percutaneously inserted with its distal end proximate the ostium. A guidewire is inserted through the guiding catheter and subselectively positioned in a region of interest in the coronary arterial tree. Multiple pressure sensors are then threaded down the guidewire and positioned in the region of interest. Advantageously, such pressure sensors are approximately 3 French in diameter, allowing multiple sensors to be threaded through the guiding catheter and positioned in the small arteries of the coronary arterial tree. Such pressure sensors can be used in conjunction with other sensors (e.g. temperature, pH, or Doppler sensors) and are useful in a variety of applications (e.g. venous, urinary tract, esophogeal). In one version of the assembly, an angioplasty catheter is fitted to the guidewire and a pressure sensor device having a small flexible catheter body is fitted to the guidewire such that inserting the angioplasty catheter into a blood vessel also pushes the pressure sensor device into the vessel.

28 Claims, 5 Drawing Sheets

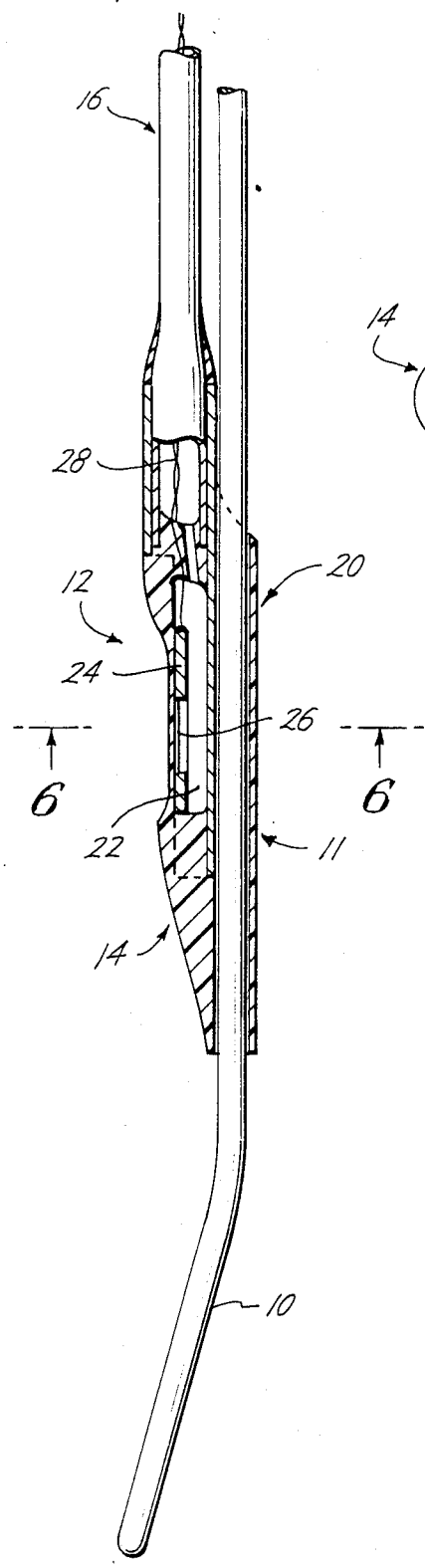
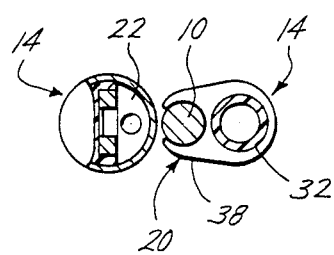
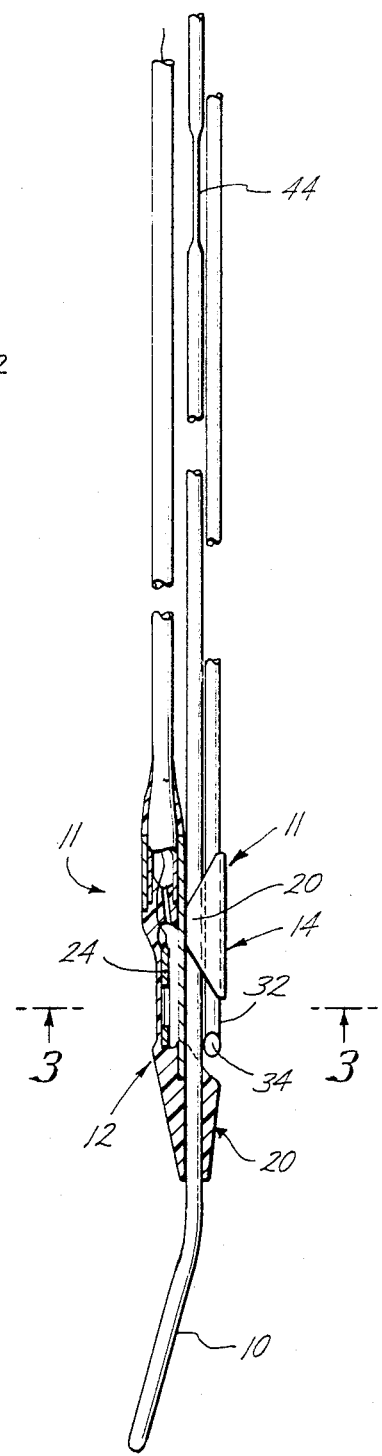

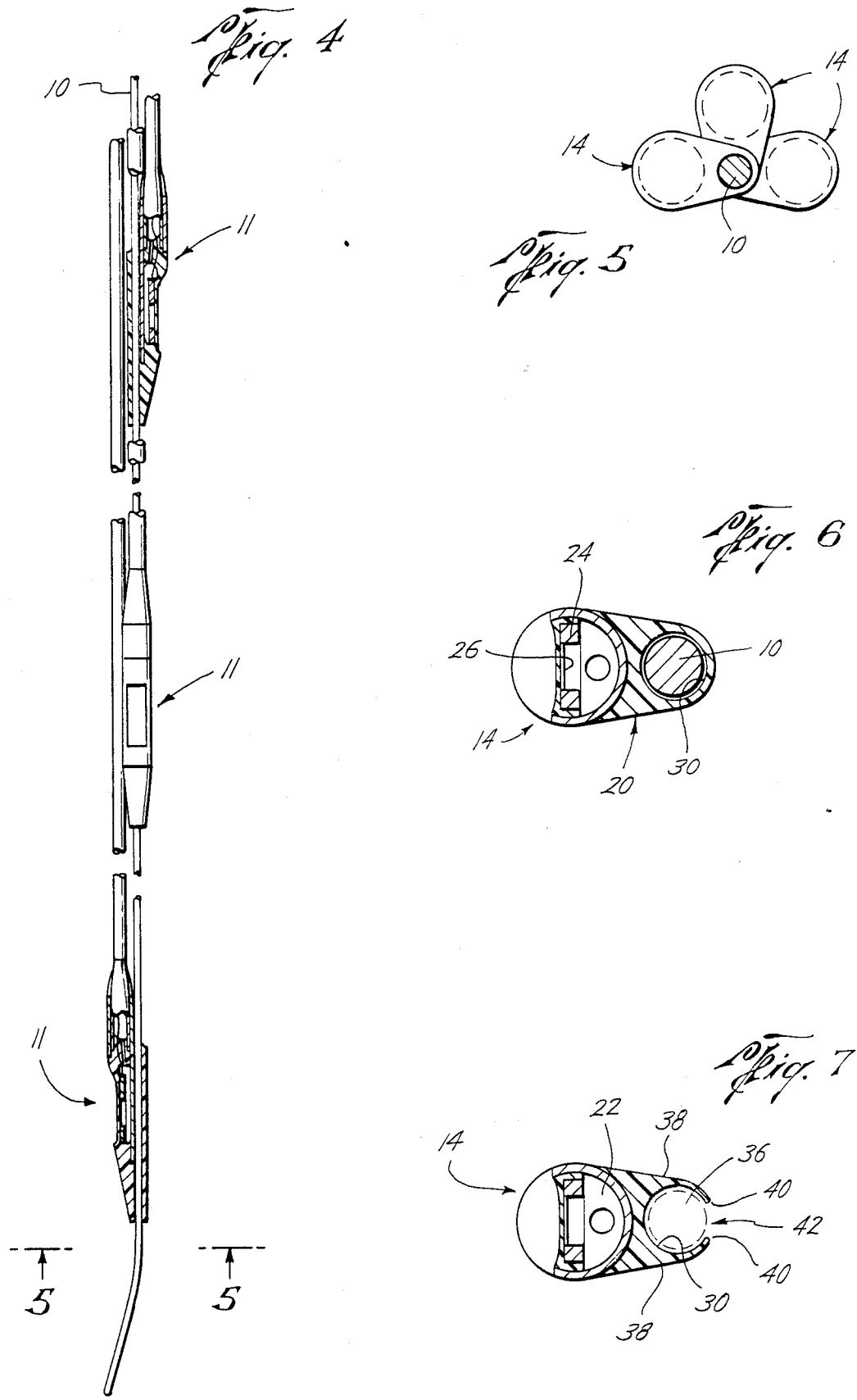

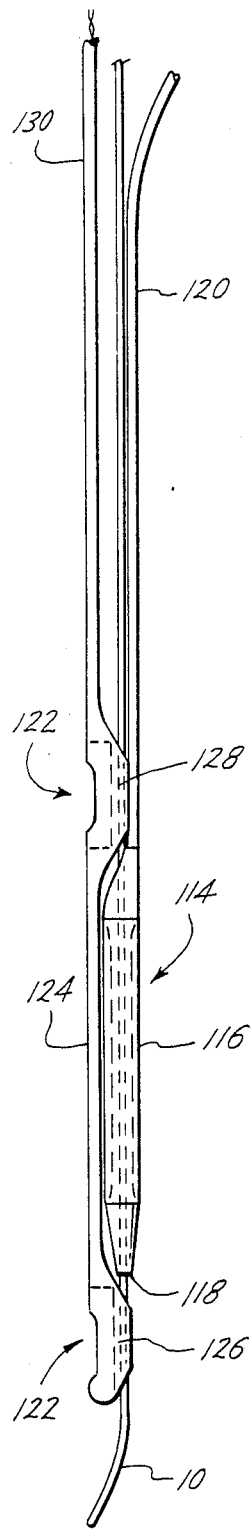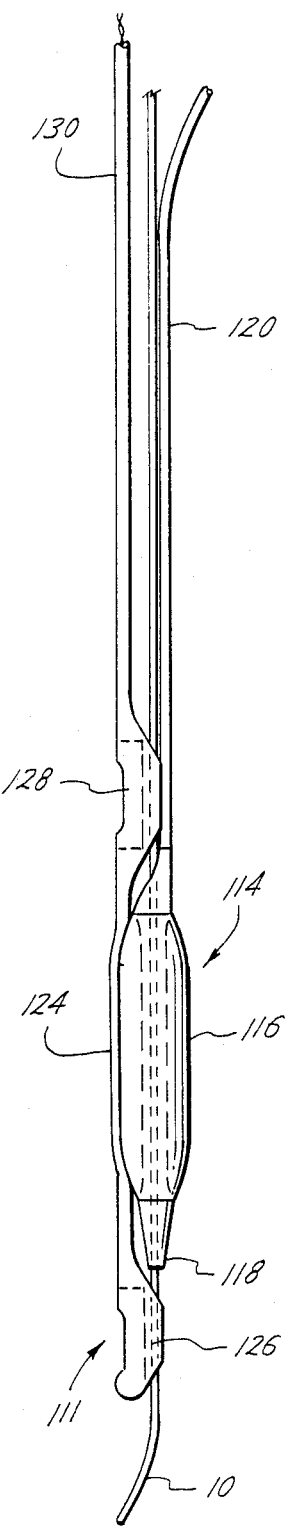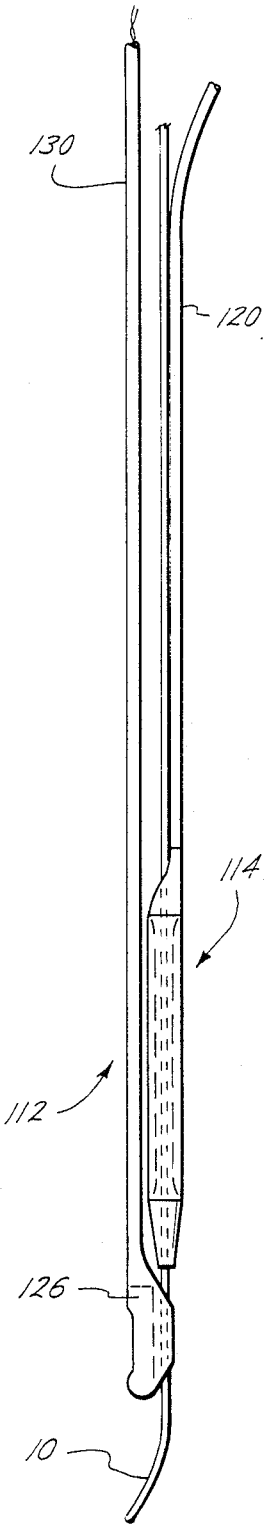

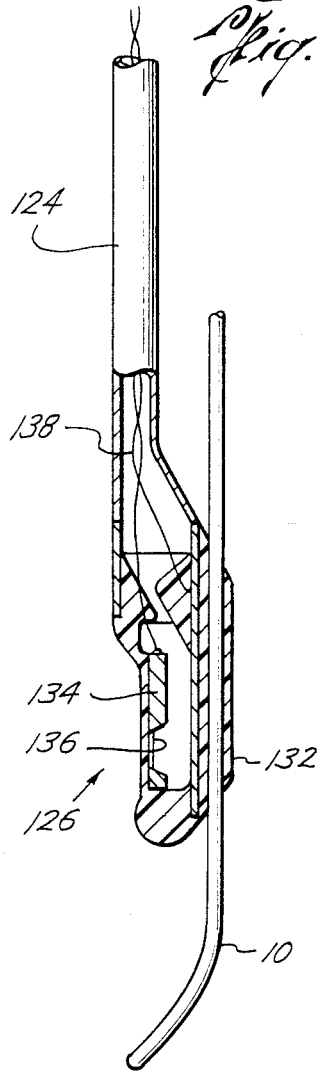
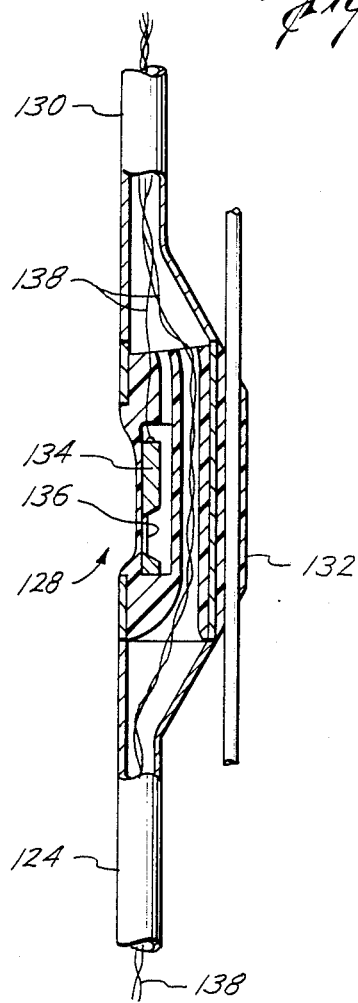
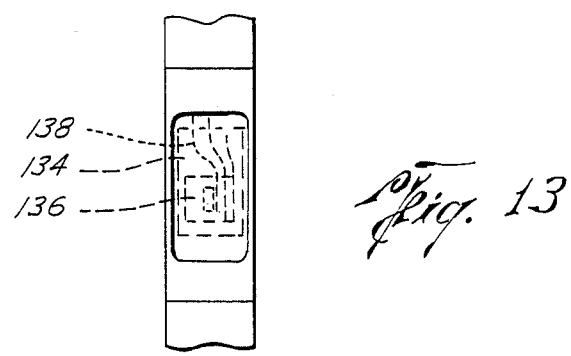

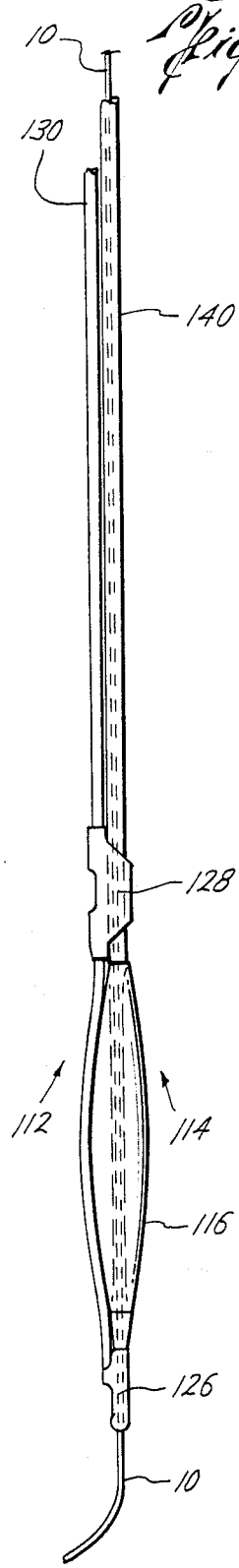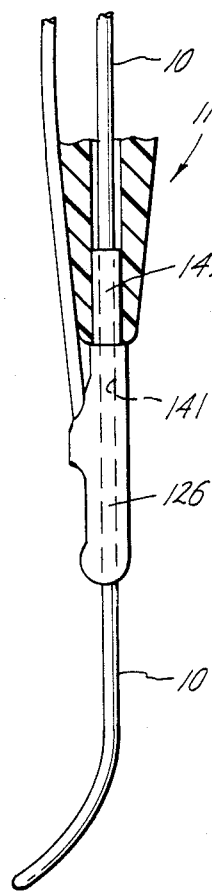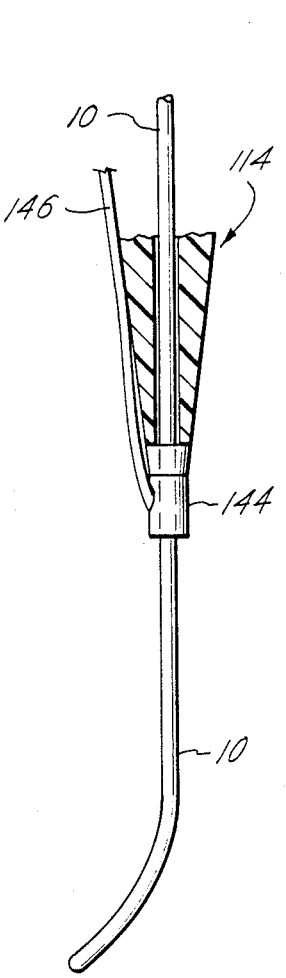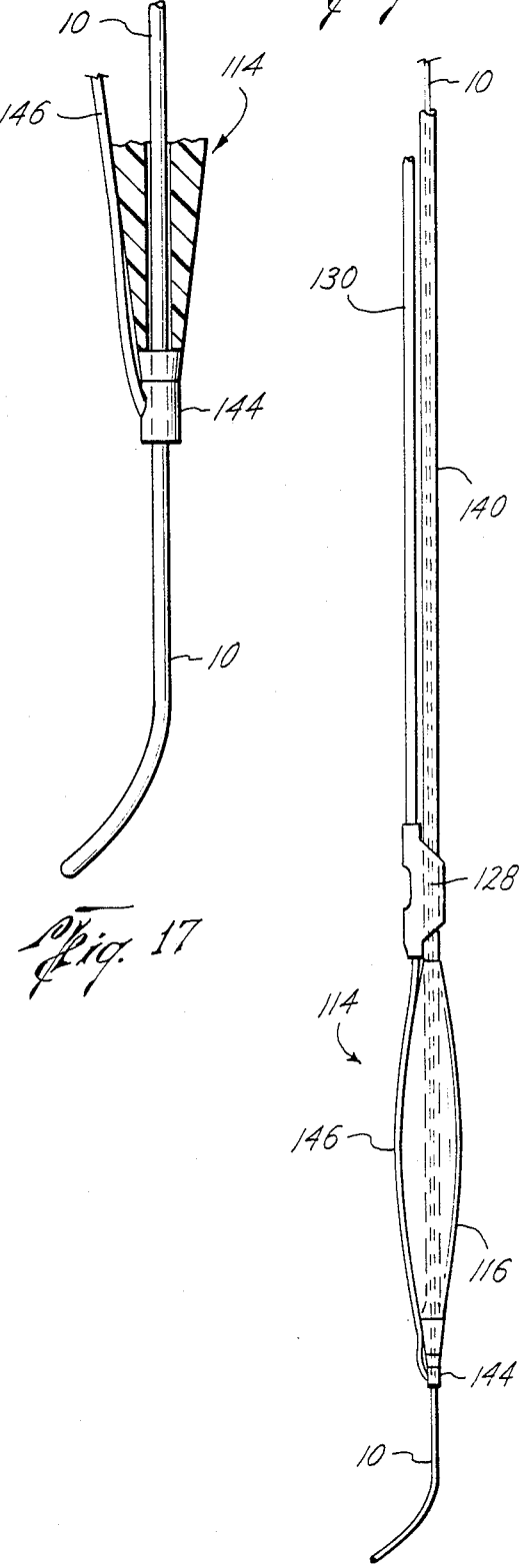

METHOD AND ASSEMBLY FOR INTRODUCING MULTIPLE DEVICES INTO A BIOLOGICAL VESSEL

BACKGROUND OF THE INVENTION

This is a continuation-in-part of Ser. No., 6/931,273 filed Nov. 14, 1986 now Pat. No. 4,771,782

FIELD OF THE INVENTION

This invention relates to a method and assembly for inserting a plurality of catheters in vivo in a biological vessel, such as a blood vessel, urethra, or the like. In one aspect, the method and assembly of the present invention contemplates a single, steerable guidewire inserted into a vessel, and one or more sensor-carrying catheters engaging the guidewire which are independently inserted into the vessel in a building block fashion. In another aspect, the present invention relates to a diagnostic device, such as a pressure sensor, that presents tethered bodies longitudinally spaced along the guidewire.

DESCRIPTION OF THE RELEVANT ART

In the past few years, there has been a sharp increase in the number of diagnostic and therapeutic procedures performed in vivo in fluid carrying biological vessels. For example, since the work of Grunzig in the late 1970's, coronary angioplasty has become a common therapeutic procedure for dilating a region of stenosis (i.e. constriction) in the coronary arteries. Coronary angioplasty is, in many cases, preferable treatment over such alternatives as open heart bypass surgery. In recent years, valvuloplasty has become an acceptable procedure for treating aortic stenosis across a heart valve.

Of course, there are a wide variety of therapeutic procedures for treating various aspects of heart disease in vivo which avoid open heart surgery. Further, diagnostic techniques, such as angiography, have become increasingly sophisticated and reliable in predicting the location and nature of heart disease. A typical angioplasty procedure usually involves a number of discrete diagnostic and therapeutic steps.

Particular problems associated with invasive diagnostic and therapeutic cardiac catheterization techniques include size restrictions of such invasive devices, which limit the ability to measure a variety of fluid characteristics. For example, pulmonary artery pressures are conventionally monitored using a flow directed catheter (e.g. Swan-Ganz catheter, see U.S. Pat. No. 3,995,623, incorporated herein by reference) which carries a pressure sensing lumen through the right ventricle into the pulmonary artery. Such right heart analysis is somewhat simplified in that Swan-Ganz catheters typically have an external diameter of about 7 French (2.3 mm), and are easily flow directed to the region of interest in the right heart.

Left heart coronary catheterization is somewhat more difficult in that any diagnostic (i.e. sensor) or therapeutic device cannot be flow directed, but must be advanced against the direction of blood flow either by direct manipulation of the catheter or by advancing it over a steerable guidewire. Conventional therapeutic and diagnostic catheter-mounted devices include a tubular catheter body having an internal lumen throughout its entire length for receiving the guidewire. U.S. Pat. Nos. 4,195,637 and 4,545,390 (incorporated herein by reference) discuss catheters and guidewires. Advancement of conventional, catheter-mounted therapeutic or diagnostic devices along a guidewire around the aortic arch to the branch points of the left and right coronary ostium is not unduly complex, and such conventional catheter-mounted devices can be sized on the order of 6 French. However, for such devices to be subselectively positionable past the coronary ostium requires an external diameter on the order of 3 French (1 mm) and an easily manipulable guidewire. The coronary arterial tree past the ostium is a prime region of interest both for diagnostic and therapeutic (e.g. angioplasty) procedures.

Difficulties with such conventional guidewire catheters having receiving lumens include: steerability of the guidewire, visualization of the coronary arteries and stenoses, and exchangeability of catheters. Exchangeability of such catheters is a particular problem (e.g. exchanging a conventional angioplasty catheter for an infusion catheter or larger angioplasty catheter) in that the distal tip of the guidewire must be maintained in the selected coronary artery while the exchange takes place. This exchange is typically accomplished using an exchange guidewire having a length (approximately 3 meters) over twice the length of the catheter so that a portion of the exchange guidewire can be held secured while the catheter is slipped over the end of the guidewire.

A major difficulty with such conventional catheters is the practical inability to carry multiple sensors, or a combination of sensors and therapeutic devices. For example, it would be preferable to avoid the necessity of exchange of conventional catheters, which might be accomplished if the catheter carried the desired variety of sensors and therapeutic devices. Such a catheter might include an angioplasty dilating balloon, an infusion lumen, a pressure sensor, a pH sensor, a temperature sensor, a fluid velocity-determining sensor, or any combination thereof. Such a complex catheter which would incorporate a wide variety of sensors and therapeutic devices would be expensive and perhaps oversized. For wide spread use, it is preferable that any invasive catheter be disposable to avoid the painstaking task of cleaning the guidewire receiving lumen or any infusing lumen which is exposed to the blood or other biological fluid. Thus, such a complex multiple device catheter would preferably be either disposable or easily cleaned and would be sized on the order of 3–4 French external diameter.

Though the heart is a primary anatomical area of interest, other anatomical regions are particularly appropriate for use of such conventional guidewire-receiving catheters for therapeutic and diagnostic use. For example, such conventional catheters are often used in the digestive tract for treating and investigating stomach disorders. Such a probe-carrying catheters might be intubated in the alimentary canal over a guidewire into the small intestine. Such probes might include balloon catheters, perfusion catheters, pH and myoelectric probes, or pressure sensors.

Another common invasive use of such guidewire-receiving catheters involves insertion of such catheters into the urinary tract. For example, a catheter carrying several pressure transducers or pressure lumens might be inserted transurethrally into the bladder and slowly withdrawn out of the urethra to determine a urethral pressure profile. As with the coronary catheters discussed above, the size of such catheters is a major restriction and the expense of such multiple sensor catheters is often prohibitive.

SUMMARY OF THE INVENTION

The problems outlined above are in large measure solved by the method and structures contemplated by the present invention. The catheters discussed above contemplate a single catheter having a guidewire-receiving lumen and perhaps one or more diagnostic or therapeutic devices. The present invention contemplates a plurality of catheters each having a coupling structure adapted for engaging a single guidewire. While conventional catheters contemplate a long lumen (e.g. 150 cm.) for slidably engaging the guidewire, the preferred embodiments of the present invention contemplates a relatively short coupling structure (e.g 1 cm) for slidably engaging the guidewire. The alternative embodiments of the present invention relate to an assembly in which one of the device has a small, flexible catheter body preferably having two tethered bodies longitudinally spaced along the guidewire.

PREFERRED EMBODIMENTS

The catheters of the preferred embodiments of the present invention do not include a guidewire-receiving lumen, and therefore the catheter body can be relatively small (e.g. less than 2 French, 0.7 mm). Preferably, the distal end of the catheter of the preferred embodiments is coupled to an elongated body carrying the diagnostic or therapeutic device. The coupling structure depends from the device-carrying body and the greatest diameter of the body and coupling structure is on the order of 3–4 French. This arrangement not only allows a plurality of device carrying catheters to be coupled to a common guidewire, but also presents a completed assembly which is still on the order of 3–4 French maximum diameter. It will be appreciated that the present invention involves a building-block approach in which a variety of sensors, probes, infusion catheters, and other diagnostic or therapeutic devices can be inserted in the vessel and selectively removed without disturbing the position of the guidewire in the vessel.

The preferred method of the present invention broadly comprises first inserting the guidewire into the vessel with the distal end of the guidewire positioned in the region of the vessel of interest. A first device is connected to the guidewire and broadly includes a body, an elongated catheter connected to the body, and a coupling structure depending from the body which is adapted for engaging the guidewire. Such a device might comprise a diagnostic pressure sensor. A second device might simply be an infusion lumen in which the body and coupling structure act merely to engage the catheter to the guidewire and to position the distal opening of the lumen in the region of interest. In most cases, the present invention contemplates that the device comprises a diagnostic tool such as a pressure sensor, temperature sensor, pH sensor, or velocity sensor.

After connecting the first device to the guidewire, the first device is inserted into the region of the vessel of interest with the coupling structure slidably engaging the guidewire. The catheter trails the body into the vessel and is generally longitudinally aligned and juxtaposed relative to the guidewire. In the preferred method of the present invention, a second device is connected to the guidewire and inserted into the vessel region in a fashion similar to the first device. The first and second devices are positioned along the guidewire in the region of interest with the respective catheters radially spaced about the guidewire.

In many applications, such as cardiac catheterization, a guiding catheter having a working lumen is first inserted into the vessel. The guidewire is then inserted through the guiding catheter into the vessel and positioned in the region of interest, with the first and second devices sequentially engaged to the guidewire and inserted through the guiding catheter into the vessel. Even though a typical cardiac catheterization guiding catheter is on the order of 8–9 French, the assembly comprising the guidewire and first and second devices is still easily threaded through the guiding catheter and positionable in the desired region.

The assembly of the preferred embodiments of the present invention include an elongated, flexible, steerable guidewire adapted for insertion into the vessel and having a distal end positionable in the region of interest. The assembly preferably includes a pressure sensor and another device, each having an elongated body, a longitudinal passage in the body for slidably receiving the guidewire, and an elongated catheter coupled to the body in longitudinal alignment therewith. The pressure sensor includes a cavity in the body which is isolated from the biological fluid when the sensor is inserted in the vessel, and a lumen in the catheter in communication with the cavity. A transducer is mounted to the body of the sensor for measuring the pressure differential between the biological fluid and the pressure within the cavity when the sensor is inserted in the vessel. The pressure sensor and other device are both adapted for sliding reception on the guidewire for positioning in the region of the vessel of interest, with the respective catheters radially spaced about the guidewire.

In one preferred form, the invention contemplates a system for introducing one or more diagnostic or therapeutic devices into the biological vessel, it being understood that a simple infusion lumen might also comprise such a device. In this embodiment, the diagnostic or therapeutic device is connected to an elongated body, and an elongated catheter is connected to the body in longitudinal alignment. A coupling mechanism depends from the body and is adapted for slidably engaging a guidewire, such that with the guidewire positioned in a biological vessel and the coupling mechanism engaging the guidewire, the body is slidable along the length of the guidewire in the vessel.

In one preferred embodiment, the coupling mechanism includes a pair of parallel fingers depending from the body and defining a guidewire-receiving groove between the fingers. The distal ends of each finger are curled towards one another to define a slot having a dimension less than the diameter of the distal section of the guidewire. Thus, the dimension of the slot prevents disengagement of the coupling mechanism from at least the distal section of the guidewire preventing inadvertent disengagement of the body from the guidewire while in the vessel.

In this embodiment, the system may include an elongated, flexible, steerable guidewire having a constricted fitting region which is outside the vessel with the guidewire positioned in the vessel. The fitting region has a transverse diameter less than the slot dimension between the fingers to facilitate engagement and disengagement of the coupling mechanism to the guidewire. As an alternative to the fitting region, the fingers of the coupling mechanism may comprise a flexible, resilient material such that the distal ends of the fingers can be spread apart and the guidewire inserted through the slot into the guidewire receiving groove.

ALTERNATIVE EMBODIMENTS

Several of the alternative embodiments of the present invention relate to an assembly of multiple devices connected to a guidewire in which one of the devices includes a pair of tethered, longitudinally spaced bodies. For example, a first device may comprise an angioplasty balloon device and the second device may comprise a proximal pressure sensor connected to a distal pressure sensor by a tether. The balloon of the first device is disposed between the two sensors with the tether bridging the balloon. The tether need not be axially rigid to insert the pressure sensor device into a blood vessel. Instead, the distal pressure sensor is configured to contact the angioplasty device, insertion of the angioplasty device effecting insertion of the pressure sensor device.

As with the preferred embodiments, the multiple devices of the alternative embodiments may comprise a variety of sensor or therapeutic devices. Advantageously, the devices are coupled to the guidewire to permit very small device sizes and the concomitant maneuvering and positional advantages. In one alternative embodiment the first device includes an elongated catheter having sufficient axial rigidity to insert the first device into the vessel, while the second device does not include such an axially rigid catheter. In this embodiment, the catheter of the second device can be made extremely small be deleting the requirement that the catheter body be sufficiently axially rigid to independently insert the second device into the vessel along the guidewire. At least a portion of the second device is located distal to the first device so that insertion of the first device pushes the second device down the guidewire.

BRIEF DESCRIPTION OF THE DRAWINGS

FIG. 1-7 illustrate the preferred embodiments of the present invention in which:

FIG. 1 is a fragmentary, elevational view of a guidewire and device in accordance with a preferred embodiment of the present invention, in which the device is in partial section depicting a pressure sensor embodiment, FIG. 2 is a fragmentary, elevational view in partial section in which the coupling structure of a first device (a pressure sensor) and a second device (an infusion lumen) are cooperatively configured to position the pressure sensor transducer and distal end of the infusion lumen in the same general location in the vessel, FIG. 3 is a vertical sectional view taken along lines 3—3 of FIG. 2, FIG. 4 is an elevational, fragmentary, view in partial section of an assembly in accordance with a preferred embodiment of the present invention showing three devices, FIG. 5 is a vertical sectional view taken along line 5—5 of FIG. 4, FIG. 6 is a vertical sectional view taken along line 6—6 of FIG. 1, and FIG. 7 is a vertical sectional view of an alternative embodiment similar to the embodiment of FIG. 6 in which the guidewire-receiving passage through the body comprises a groove; and FIG. 8-17 depict the alternative embodiments of the present invention in which:

FIG. 8 is a fragmentary, elevational view in which the first device comprises angioplasty balloon and the second device includes a pair of spaced pressure sensors, FIG. 9 is a fragmentary, elevational view similar to FIG. 8 in which the angioplasty balloon is inflated, FIG. 10 is a fragmentary elevational view similar to FIG. 8 in which the second device comprises a single pressure sensor, FIG. 11 is an enlarged, fragmentary view in partial section of the distal pressure sensor of FIGS. 8, 9, and 10, FIG. 12 is a fragmentary view in partial section of the proximal pressure sensor of FIGS. 8 and 9, FIG. 13 is a fragmentary, elevational view with parts shown in phantom of the pressure transducer of FIG. 12, FIG. 14 is a fragmentary, elevational view of an assembly similar to FIG. 8 in which the first device includes an elongated catheter body in which the guidewire is received internally and the proximal pressure sensor of the second device is coupled to the catheter body, FIG. 15 is an enlarged, fragmentary view in partial section illustrating the distal pressure sensor of the assembly of FIG. 13, FIG. 16 is a fragmentary, elevational view of another alternative embodiment in which the second device comprises a single, proximal pressure sensor, and FIG. 17 is an enlarged, fragmentary view in partial section of the distal engagement structure of FIG. 16.

DESCRIPTION OF THE PREFERRED EMBODIMENTS

Turning now to FIGS. 1-7, an elongated, flexible guidewire 10 is shown which is insertable into a biological vessel. In FIG. 1, the guidewire is particularly adapted for cardiac catheterization and is approximately 0.014 inches (0.3 mm) in outer diameter. In the drawing, a plurality of diagnostic devices 11 are shown coupled to the guidewire 10. In FIG. 1, a single device 11 includes a pressure sensor 12 similar to Model No. SPC-350 as sold by Millar Instruments, Inc. of Houston, Tex.

Broadly speaking, each device 11 includes an elongated body 14, and elongated catheter 16 coupled to the body 14 in longitudinal alignment therewith and coupling mechanism 20 depending from the body 16.

In more detail, the body 14 of the pressure sensor 12 includes an internal cavity 22 which is isolated from the biological fluid with the sensor 12 immersed in the fluid. An elongated, rectangular pressure member 24 is mounted along one wall of the body 14 and includes a thin, flexible diaphragm 26. With the sensor 12 inserted into biological fluid the diaphragm 26 is flexed in response to the pressure of the fluid. In most cases, the cavity 22 is simply filled with ambient air so that the diaphragm 26 deforms in response to differential pressure between the biological fluid pressure and ambient air pressure. Strain gauges (not shown) are coupled across the diaphragm and are responsive to the flexure of the diaphragm 26. Electrical leads 28 are coupled to the strain gauges and lead through the catheter to an external electronic processing device.

Viewing FIGS. 1 and 6, the coupling mechanism 20 depends from the body 14 and defines an elongated passage 30 for slidably receiving the guidewire 10 as shown in FIG. 1. The diameter of the passage 30 is approximately 0.016 inches so that the guidewire 10 is easily slidable therethrough. Overall, the largest dimension of the body 14 and coupling mechanism 20 (the vertical dimension as depicted in FIG. 6) is approximately 3-4 French or slightly in excess of 1 mm.

Turning to FIGS. 2-5 and 7, a variety of alternatives and modifications are illustrated, the same numerals being applied for the structures illustrated in FIG. 2-5 and 7 as applied to the embodiment illustrated in FIG. 1 and 6. In FIG. 2 a guidewire 10 is illustrated in which two different devices 11 are mounted. For illustrative purposes, the first device comprises a pressure sensor 12 similar to the pressure sensor 12 illustrated in FIG. 1. The second device in FIG. 2 comprises an infusion catheter 32 which provides a working lumen having a distal opening 34.

The pressure sensor 12 has been modified in FIG. 2 in that the coupling mechanism 20 is truncated and located to depend from the distal end of the body 14. As can be seen in FIG. 2, the coupling mechanism 20 of the infusion catheter 32 is located such that the distal opening of the lumen 34 is located in the same general axial location (transverse plane of the biological vessel) as the sensor member 24 of the pressure sensor 12. It will be appreciated that two or more devices 11 may have their coupling mechanisms 20 spaced relative to their sensor portions (e.g. sensor member 24), such that the devices 11 may be positioned with the sensors in the same general transverse cross-section in the biological vessel. For example, a first pressure sensor 12 may have its coupling mechanism 20 located at its distal end (as shown in FIG. 2), a second pressure sensor 12 may have its coupling mechanism 20 located in a medial location, while a third pressure sensor 12 may have a coupling mechanism 20 located in a proximal position on the body 14. The location of the coupling mechanisms 20 on their respective pressure sensors 12 permit the pressure sensors 12 to be all positioned on the guidewire 1 such that the three pressure sensor members 24 are in the same general location (transverse cross-section) in the vessel.

As shown more clearly in FIG. 3, the coupling mechanism 20 of the infusion catheter 32 is another embodiment in which the passage 30 is not a cylindrical bore as shown in FIG. 6, but instead comprises a groove 36 as shown with more clarity in FIG. 7. As can be seen from FIG. 7, this embodiment of the coupling mechanism 20 comprises a pair of depending fingers 38 which define therebetween a guidewire receiving groove 36. The distal tips 40 of the fingers 38 curl back towards one another to define a slot 42 therebetween. As can be appreciated from FIG. 7, the dimension of the slot 42 defined between the distal tips 40 is less than the outer diameter of the wire guide 10. In FIG. 7, the fingers 38 comprise a flexible, resilient material such that the tips 40 can be spread apart for receiving the guidewire 10.

FIG. 2 illustrates a variation of the guidewire 10 in that a constricted fitting region 44 is illustrated. In the embodiment of FIG. 2, the guidewire 10 includes a distal section which is designed for insertion into the vessel, and a proximal section which is intended to remain outside of the body during normal use. The fitting region 44 is located in the proximal section and preferably simply comprises a constricted, cylindrical portion of the guidewire 10 having a reduced diameter. Preferably, the diameter is approximately the dimension of the slot 42 to facilitate engagement of the coupling mechanism 20 to the guidewire 10. In an alternative form, the fitting region 44 simply comprises two parallel, flat regions on opposing sides of the guidewire 10, with the distance between the flat regions approximately the dimension of the slot 42. In FIG. 3, the fingers 38 are not necessarily flexible, and are preferably not spread apart so that coupling to the guidewire 10 can only occur in fitting region 44.

Turning to FIGS. 4 and 5, an assembly is illustrated in which three devices 11 are slidably mounted to the guidewire 10. In FIG. 4, each device 11 comprises a pressure sensor 12 identical to the pressure sensor 12 illustrated in FIGURE 1. As can be perhaps best seen in FIG. 5, the pressure sensors 12 are radially mounted about the guidewire 10. Of course, the respective catheter 16 of each sensor 12 trails the respective body 14 with each catheter 16 generally longitudinally aligned and juxtaposed adjacent the guidewire 10. As can be seen in FIG. 4, in this embodiment the devices 11 are longitudinally spaced along the guidewire 10 and would be useful, for example, in determining a pressure gradient along a longitudinal region of the vessel.

Operation of the Preferred Embodiments

Broadly speaking, the method of the present invention contemplates analyzing in vivo a biological fluid in a region of a biological fluid-carrying vessel. As an example, a hypothetical coronary angioplasty procedure will be described in which the stenosed coronary artery is located in the arterial tree past the left coronary ostium. Broadly speaking, such an angioplasty procedure might involve inserting a guiding catheter (7-8 French Sheath) through the femoral artery approach as is well known in the art. Preferably, the guidewire is advanced to a region close to the root of the ascending aortic arch. As the guidewire is advanced, several devices 11 are coupled to the guidewire 10 to assist in advancement and visualization of the position of the guidewire 10. The first device 11 may comprise an angioplasty dilating balloon in combination with a velocity-determining sensor, similar to that described in U.S. Pat. No. 4,665,925 (incorporated herein by reference). In this example, the first device 11 would include an angioplasty balloon mounted to the body 14 with the pneumatic lumen running through the catheter 16. A Doppler crystal would be fitted to the distal end of the body 14 with the electrical leads running through the catheter 16. As can be appreciated from the drawing, the streamline, low profile configuration of the body 14 aides in manipulating the device 11 past constrictions in the approach.

A second device 11 would, in this example, comprise an infusion catheter 32 as illustrated in FIG. 2 which could be used for injecting contrast medium for positioning of the guidewire 10 and devices 11 as they are advanced. Additionally, the infusion catheter 32 could be used for transcatheter pressure readings as desired. Finally, a third device 11 comprising a pressure sensor 12 would be advanced which, in most cases, would be helpful in positioning the guidewire 10 and devices 11. Other devices 11, such as pH or temperature probes, might similarly be mounted to the guidewire 10 and advanced perhaps through the aortic arch.

Eventually, the guidewire 10 is advanced to intubate the left coronary ostium using a conventional method such as the Judkins technique. The distal tip of the guidewire 10 is then manipulated and steered into the coronary artery of interest, with the stenosis identified using a variety of techniques, such as the arteriogram, fluid velocity measurements, and perhaps fluid pressure measurements. With the guidewire 10 positioned in the region of stenosis, the angioplasty balloon can be inflated to distend the stenosis and the efficacy of the treatment analyzed using one or more of the devices 11.

Assuming, that one of the devices 11 initially advanced towards the coronary arteries is to be replaced, such exchange of devices 11 is easily accomplished in accordance with the method of the present invention. For example, the first or distal device 11 and guidewire 10 are left in position in the region of the coronary artery of interest and the second device 11 is to be exchanged. The second and subsequent devices 11 can be withdrawn and once outside the body are easily slid from the guidewire 10.

In the embodiments of FIGS. 2, 3, and 7, exchange is even easier. For example, the third and successive devices 11 are slid along the guidewire 10 proximal to the fitting region 44 and the second device 11 slid into the fitting region 44 and easily disengaged from the guidewire 10. Of course, if the coupling mechanism 20 comprises flexible resilient fingers 38 (FIG. 7), then a fitting region 44 is not necessary for decoupling the device 11. With the third and successive devices 11 spaced from the body (or proximal to the fitting region 44) a substitute second device 11 is easily coupled to the guidewire 10 ahead of the third and successive devices 11 and reinserted along the guidewire 10 into the fluid-carrying vessel. As can be appreciated, such exchange of devices 11 is clinically advantageous in terms of speed and maintenance of the position of the guidewire 10 in the diseased region of the coronary artery.

Of course, many other uses of the method and assembly of the present invention are contemplated. For example, valvuloplasty has become a common procedure for treating stenosis across a heart valve. In such a procedure, the guidewire 10 is advanced along the guidewire into the ventricle with a pressure sensor 12 advanced into the ventricle. A second device 11, comprising an angioplasty balloon catheter, is advanced over the guidewire 10 and positioned in the region of the heart valve. Subsequently, another pressure sensor 12 might be advanced behind the balloon catheter. In this procedure, the balloon is expanded and the aortic valve distended to relieve the stenosis.

Another application involves the use of such an assembly in accordance with the present invention in the diagnosis and perhaps treatment of urinary track abnormalities. For example, urinary incontinence might be diagnosed with the guidewire 10 advanced through the urethra into the bladder and a first pressure sensor 12 advanced along the guidewire 10 into the bladder. A second pressure sensor 12 might then be advanced along the guidewire 10 into the urethra and bladder pressure and urethra pressure monitored. Other devices 11 might similarly be advanced for monitoring temperature, pH or velocity of the urine.

Still another application might involve diagnosis of acidity and peristaltic action of the digestive tract. In such diagnosis, the guidewire 10 would be advanced past the esophageal valve and the distal end positioned in the stomach. A first device 11, comprising a pH sensor and perhaps a pressure sensor 12 is advanced through the valve into the stomach to monitor the acidity and pressure in the stomach. A second pressure sensor 12 is then inserted into the esophageal tract above the esophageal valve. Thus, the two pressure sensors could monitor the efficacy of the esophageal valve.

As can be appreciated from the above discussion, sensors such as pressure sensors, velocity measuring sensors, pH and temperature probes, etc. can be expensive. Under current technology, all such sensors or therapeutic devices must be incorporated into a single catheter which can be very expensive. In most cases, it is necessary that such a catheter have a working lumen to allow access to the fluid vessel for injecting contrast media, monitoring pressure, or to perform similar functions. Such a working lumen is, of course, contaminated with the blood or other biological fluid and must be thoroughly cleaned if the multiple device catheter is to be reused. In view of the contamination and difficulty in cleaning, there is a strong bias towards disposable catheters. However, such a multiple sensor catheter is very expensive and not readily amenable to manufacturing as a disposable item. Often times, if such a multiple sensor catheter is produced, the sensors are manufactured in such a fashion to reduce cost with limited improvement in fidelity.

Using the method and assembly of the present invention, a favorable alternative exists. That is, the expensive devices 11 such as the sensors, can be high fidelity instruments designed for reuse. In such a situation, the infusion catheter 32 would be a low cost disposable item in view of the difficulty of adequately and efficiently cleaning the lumen of the infusion catheter 32. In the assembly of the present invention, the lumen of the catheter 16 is isolated from the fluid, so that only the external surfaces of the catheter 16 and body 14 must be cleaned a relatively simple task. The relatively short passage 30 of the coupling mechanism 20 is readily cleaned, and in the alternative embodiment (FIGS. 2, 3, 7) comprising the groove 36, is especially easily cleaned for reuse. Thus, the high fidelity sensor-type devices 11 can be designed for reuse and the high cost of such devices 11 amortized over a number of procedures and a number of patients.

Description of Alternative Embodiments

Turning to FIGS. 8–17, an elongated flexible guidewire 10 is shown which is insertable into a biological vessel and a plurality of devices 111 are couplable to the guidewire 10 for insertion into the biological vessel. In FIGS. 8–9 one of the devices 111 comprises a pressure sensor device 112, while the other device comprises an angioplasty device 114. In FIG. 8, the angioplasty device 114 is similar to commercially available devices, such as a Schneider-Medintag AG, Zurich Switzerland, Monorail-Bonzel coronary dilation catheter (e.g. Model Nos. Sch-30230, Sch-30280, Sch-30220).

In more detail, the angioplasty device 114 includes a balloon 116 and a coupling mechanism 118 running through the balloon 116 for receiving the guidewire 10. An elongated catheter 120 runs proximal from the coupling mechanism 118 and is, of course, of sufficient length to run outside the patient's body with the angioplasty device 114 inserted in a biological vessel of the patient. The catheter 120 is not coupled to the guidewire 10, but does contain at least a pneumatic lumen for inflation of the balloon 116. Further, the catheter 120 has sufficient axial rigidity for inserting the angioplasty device 114 into the biological vessel.

The pressure device 112 (FIGS. 8 and 9) broadly comprises a pair of longitudinally spaced apart bodies 122 and are connected by a tether 124. In the embodiment of FIGS. 8 and 9, the bodies 122 comprise a distal pressure sensor 126 and a proximal pressure sensor 128. An elongated catheter 130 is connected to the proximal pressure sensor 128 and is of sufficient length to run outside the patient's body With the pressure device 112 inserted in the biological vessel. The catheter 130 defines a lumen for supplying a reference pressure (preferably atmospheric pressure) to the pressure sensors 126, 128. The catheter 130 comprises a thin-walled flexible material to reduce the amount of space the catheter 130 requires in the biological vessel. The catheter 130 lacks sufficient axial rigidity for insertion into the biological vessel along the guidewire 10 independently. That is, the catheter 120 is relatively rigid in comparison to the catheter 130.

Turning to FIG. 10, the assembly illustrated very similar to the assembly of FIGS. 8 and 9, with a difference in the structure of the pressure device 112. In the assembly of FIGURE 10, the pressure device 112 comprises a single distal pressure sensor 126 in which the catheter 130 is connected directly to the distal pressure sensor 126. That is, the pressure device 112 of FIG. 10 lacks the proximal pressure sensor 128 illustrated in FIGS. 8 and 9.

Turning to FIGS. 11–13 the pressure sensors 126, 128 are illustrated in more detail. Each pressure sensor 126, 128 includes a depending coupling mechanism 132 for engaging the guidewire 10. The coupling mechanism 132 may comprise any of the coupling mechanisms 20 illustrated in the preferred embodiments in FIGS. 1–7. As can be seen from FIGS. 11–12, the depicted coupling mechanism 132 is nearly identical to the coupling mechanism illustrated in FIG. 6 in which the coupling mechanism defines a passage for receiving the guidewire 10. However, it will be understood that the coupling mechanism 132 of FIGS. 11–12 may comprise a pair of spaced apart fingers defining a groove as shown in FIG. 7 for lateral snap-on coupling of the pressure sensors 126, 128 to the guidewire 10.

The pressure sensors 126, 128 each include a pressure transducer 134 similar to Model No. SPC-350 as sold by Millar Instruments, Inc. of Houston, Texas. FIG. 13 illustrates the pressure transducer of the proximal pressure sensor 128 in more detail. Each pressure transducer 134 preferably comprises a semiconductor material having a weakened diaphragm region 136. Strain gauges are mounted to measure movement of the diaphragm 136 and are coupled to leads 138.

As can be seen from FIGS. 11 and 12, the pressure transducers 134 are mounted such that one surface faces outwardly to respond to the biological fluid pressure with the device 112 inserted in a biological vessel. The opposing (inward) surface of the pressure transducers 134 are exposed to a reference fluid pressure so that the diaphragm 136 flexes in response to a differential between the biological fluid pressure and the reference fluid pressure. In this regard, the catheters 130 and tether 124 define pressure lumens for supplying the reference pressure to the respective pressure transducers 134, in this case atmospheric pressure.

Turning to FIGS. 14–15, still another alternative embodiment is illustrated in which the angioplasty device 114 is of a different configuration. In the embodiments illustrated in FIGS. 14–17, the angioplasty device 114 includes an elongated catheter 140 of a conventional design in which the guidewire 10 is received in the guidewire receiving passage within the catheter 140. Such angioplasty devices 114 illustrated in FIGS. 14–17 are similar to angioplasty devices such as sold by USCI (Model No. 006646), ACS (Model No. 11051) and Schneider-Shiley (Model No. Sch-30242). In the embodiments of FIGS. 14–17, the proximal pressure sensor 128 is modified to couple to the exterior of the catheter 140. In FIGS. 14–17 the coupling mechanism of the proximal pressure senor 128 preferably defines a catheter receiving passage similar to that illustrated in FIG. 6, it being understood that the coupling mechanism illustrated in FIG. 7 is a viable alternative.

In FIGS. 14–15, the distal pressure sensor 126 is also changed from the embodiments of FIGS. 8–10. As shown in more detail in FIGURE 15, the distal pressure sensor 126 defines an elongated guidewire-receiving passage 141 therethrough as shown in phantom in FIG. 15. Pressure sensor 126 includes tubular journal 142, which is an extension of this guidewire receiving passage and is slidably receivable within the central passage of the angioplasty device 114. Advantageously, with the tubular journal 142 coupled to the angioplasty device 114 the guidewire 10 may be withdrawn and the distal pressure sensor 126 remains coupled to the angioplasty device 114.

Turning to FIGS. 16–17, still another alternative embodiment is illustrated which contains only a single proximal pressure sensor 128. In FIGS. 16–17, a connection structure 144 is coupled to the guidewire 10 distal to the angioplasty device 114. The connection structure 144 is interconnected to the proximal pressure sensor 128 via a link or tether 146. The tether 146 has no requirement for a reference pressure lumen. Further, the connection structure 144 (FIG. 17) omits the tubular journal 142 (FIG. 15) such that the connection structure 144 simply abuts the angioplasty device 114. Advantageously, the cross-sectional dimension of the devices 112, 114 may be tapered from the connection structure 144 to the pressure sensor 128.

FIGS. 14–17 also illustrate a utility of the present invention in another type of application with the guidewire 10 removed. That is, the balloon 116 may comprise a flotation balloon, such as a Swan-Ganz flow directed catheter made by Edwards Laboratories of Santa Ana, California. In such right heart placement, the devices 112, 114 are advanced (preferably along guidewire 10) through the selected vein proximate the right atrium. The flotation balloon 116 is inflated, carrying both devices 112, 114 into the right ventricle and preferably into the pulmonary artery.

In such a right heart application the catheter 140 preferably has sufficient axial rigidity for advancement of the devices 112, 114 proximate to the right atrium. Preferably the catheter 130 is thin and flexible (less rigid than catheter 140) to easily trail device 114 as it advances into the pulmonary artery. With the guidewire 10 missing, a working lumen is provided for pressure measurements, perfusion or other purposes.

Operation of the Alternative Embodiments

The operation and advantages of the alternative embodiments illustrated in FIGS. 8–17 is very similar to the operation of the preferred embodiments of FIGS. 1–7. However, in the alternative embodiments the devices 111 are preferably coupled to the guidewire 10 and inserted as a unit into the biological vessel. That is, the catheters 120, 140 of the angioplasty devices 114 have sufficient axial rigidity to insert the multiple devices 111 into the biological vessel. Of course, the devices 111 may encounter restrictions such as stenosed coronary arteries during insertion. While the catheter 130 of the pressure device 112 lacks axial rigidity sufficient for insertion independently, engagement of the angioplasty device 114 with the pressure device 112 pushes the pressure device 112 through the biological vessel with the catheter 130 simply trailing into the biological vessel.

As illustrated in FIGS. 8-10, the distal end of the angioplasty device 114 engages the distal pressure sensor 126 to push the device 112 during insertion. Withdrawal of devices 112, 114 from a biological vessel is simply a matter of pulling on catheters 130, 120 (or both). As illustrated in FIG. 9 during an angioplasty procedure, the balloon 116 is outwardly expandable and in some cases deflects the tether 124 (or the catheter 130 of FIG. 10) during expansion. Of course, the tether 124 bridging the balloon 116 is flexible enough to deform during angioplasty expansion. Advantageously, during use the pressure sensors 126, 128 measure the pressure differential on each side of the balloon 116. This is particularly advantageous during an angioplasty or valvuloplasty procedure.

The operation of the embodiments of FIGS. 16-17 is very similar to the operation of the embodiments of FIGS. 8-10. In FIGS. 16-17, the distal pressure sensor 126 is eliminated, so advancement of the pressure device 112 is made by engagement of distal end of angioplasty device 114 with the connection structure 144. Withdrawal of the devices 112, 114 is fairly easy from the biological vessel in that pulling motions on either or both of the catheters 130, 140 will withdraw devices 112, 114 from the biological vessel.

The embodiment illustrated in FIGS. 14-15 has an added advantage in that the tubular journal 142 assures connection of the distal pressure sensor 126 to the angioplasty device 114. After the devices 112, 114 are inserted into the biological vessel, the guidewire 10 can be withdrawn, with the distal pressure sensor 126 remaining fixed relative to the angioplasty device 114. With the guidewire 10 withdrawn, the guidewire-receiving passageway through the devices 112, 114 can be used for other purposes, such as an infusion lumen or a fluid filled pressure sensing lumen.

In the above discussion of FIGS. 8-17, the devices 111 comprise a pressure device 112 and angioplasty device 114. However, it will be understood that as in the preferred embodiments of FIGS. 1-7, other types of diagnostic and therapeutic devices are possible without departing from the scope of the present invention as defined by the claims.

As can be appreciated from the above discussion, the method, pressure sensor, assembly and system of the present invention present a marked practical advance over conventional catheterization methods in more efficient diagnoses and treatment in vivo.

What is claimed is:

1. A pressure sensor adapted for engaging an elongated element such as a guidewire or the like, comprising:
    a distal and a proximal body, the distal body having means for engaging the element;
    a pressure transducer coupled to at least one of the bodies;
    an elongated catheter coupled to the proximal body; and
    an elongated tether connecting the bodies adapted for allowing longitudinal spacing of the bodies along the element with the tether generally parallel and disposed along the element.

2. A pressure sensor according to claim 1, the proximal body including means for engaging the element.

3. A pressure sensor according to claim 1, the proximal body including means for engaging another catheter disposed along the element.

4. A pressure sensor according to claim 1, each body including a pressure transducer and a cavity adapted to remain in isolation from biological fluid with the sensor inserted in a biological fluid-filled vessel.

5. A pressure sensor according to claim 4, the tether including a lumen connecting the cavities and the catheter including a lumen in communication with the proximal cavity.

6. An assembly for engaging an elongated, flexible, steerable guidewire insertable in a biological fluid-carrying vessel and having a distal end positionable in a region of the vessel, the assembly comprising:
    a first device adapted for engaging the guidewire and positionable in the region, the device including
        an elongated member,
        coupling structure connected to the member defining a passage longitudinally oriented with the member for slidably receiving the guidewire,
        an elongated catheter coupled to the member in longitudinal alignment therewith;
    a second device adapted for engaging the guidewire and positionable in the region, the second device including
        distal and proximal bodies adapted for positioning along the guidewire in longitudinally-spaced relation distal and proximal to said member respectively,
        engagement structure connected to the distal body for slidably receiving the guidewire and adapted to contact the distal end of said member,
        an elongated catheter coupled to the proximal body,
        tether means operably connecting the distal and proximal bodies,
    the first and second devices being adapted for reception on the guidewire in the region of the vessel.

7. The assembly according to claim 6, the coupling structure defining an elongated lumen in the catheter of the first device for receiving the guidewire.

8. The assembly according to claim 6, the coupling structure depending from the member and defining a passage for receiving the guidewire.

9. The assembly according to claim 6, the coupling structure comprising a guidewire-receiving groove defined by a pair of spaced-apart fingers.

10. The assembly according to claim 1, the engagement structure comprising a guidewire-receiving groove defined by a pair of spaced-apart fingers.

11. The assembly according to claim 1, the engagement structure depending from the distal body and defining a passage for receiving the guidewire.

12. The assembly according to claim 1, at least one of the bodies comprising a pressure sensor.

13. The assembly according to claim 12, the distal body including a pressure sensor having an internal cavity, the tether including a lumen communicating the cavity with a lumen in the catheter of the second device.

14. The assembly according to claim 1, the engagement structure including a journal adapted to interfit the passage of the coupling structure.

15. The assembly according to claim 6, the member comprising a balloon, the tether means being transversely flexible and displaceable during balloon inflation.

16. The assembly according to claim 1, the catheter of the first device being sufficiently axially rigid for inserting the first device in the vessel coupled to the guidewire.

17. The assembly according to claim 16, the catheter of the second device having an axial rigidity less than the catheter of the first device, the second device disposed relative to the first device for simultaneous insertion therewith.

18. A method of placing one or more devices in a region of a biological fluid-carrying vessel, comprising the steps of:
   inserting an elongated, flexible guidewire into the vessel with a portion of the guidewire extending into the region;
   providing a first device having an elongated catheter, a member connected to a distal end of the catheter, and a coupling structure adapted for engaging the guidewire;
   connecting to the guidewire a second device having distal and proximal bodies, an elongated catheter connected to the proximal body, an engagement structure connected to the distal body and adapted for engaging the guidewire and for contacting the member of the first device, and a tether interconnecting the bodies;
   connecting to the guidewire the first device so that the distal and proximal bodies are spaced distal and proximal to the member respectively;
   inserting the first and second devices into the vessel region with the coupling structure and engagement structure slidably engaging the guidewire and the catheters generally longitudinally aligned and juxtaposed relative to the guidewire, including the substep of,
      advancing one of the catheters to insert the one device into the vessel where one of the bodies contacts the member to simultaneously insert the other device into the vessel.

19. The method according to claim 18, wherein one of the devices includes a pressure sensor, the method including the step of determining the pressure of the biological fluid in the region of the pressure sensor.

20. The method according to claim 18, the coupling structure defining an elongated lumen within the catheter for receiving the guidewire, the second device connecting step including the substep of coupling the engagement structure to the guidewire and the proximal body to the catheter.

21. The method according to claim 18, the engagement structure of the second device comprising a pair of spaced-apart fingers defining an elongated, guidewire receiving groove, including the step of disconnecting the second device by withdrawing the first and second devices from the vessel and shifting the guidewire from the groove in a direction transverse to the longitudinal axis of the groove.

22. The method according to claim 18, including the steps of:
   providing a guidewire having a constricted fitting region located outside the vessel with said portion of the guidewire extending into the region;
   providing the second device with an engagement structure comprising a pair of spaced-apart fingers defining a guidewire-receiving groove,
   connecting the guidewire to the second device by shifting the fitting region between the fingers into the groove.

23. The method according to claim 22, the fingers comprising a generally inflexible material, inserting the second device into the vessel along the guidewire past the fitting region effecting slidable, locking engagement of the fingers about the guidewire.

24. The method according to claim 18, the first device having a relatively axially rigid catheter and the second device having a relatively flexible catheter, the inserting step comprising the substeps of advancing the catheter of the first device and contacting the distal body of the second device with the member of the first device to advance the second device along with the first device in the vessel.

25. An assembly for engaging an elongated, flexible, steerable guidewire insertable in a biological fluid-carrying vessel and having a distal end positionable in a region of the vessel, the assembly comprising:
   a first device adapted for engaging the guidewire and positionable in the region, the device including
      an elongated member,
      coupling structure connected to the member defining a passage longitudinally oriented with the member for slidably receiving the guidewire,
      an elongated catheter coupled to the member in longitudinal alignment therewith;
   a second device having a distal body adapted for engaging the guidewire distal to the first device and positionable in the region, the second device including
      engagement means connected to the distal body for slidably receiving the guidewire and adapted to contact the distal end of said member of the first device, and
      an elongated catheter coupled to the body;
   the catheter of the first device being relatively axially rigid and the catheter of the second device being relatively flexible; such that when the devices are coupled to the guidewire, advancement of the first catheter places the member in contact with the distal body advancing the second device along the guidewire.

26. The assembly according to claim 25, the second device including another body adapted to be positioned proximal to said member when the devices are engaging a guidewire.

27. The assembly according to claim 26, one of the bodies comprising a pressure sensor.

28. A method of placing one or more devices in a region of a biological fluid-carrying vessel, comprising the steps of:
   inserting an elongated, flexible guidewire into the vessel with the distal end of the guidewire extending into the region;
   connecting to the guidewire a first device having an elongated catheter, a member connected to one end of the catheter, and a coupling structure adapted for engaging the guidewire;
   connecting to the guidewire a second device having an elongated body, an elongated, relatively flexible catheter connected to the body, and an engagement structure connected to the body for engaging the guidewire and for contacting the member of the first device;

inserting the first and second devices into the vessel region with the coupling structure and engagement structure slidably engaging the guidewire and the catheters generally longitudinally aligned and juxtaposed relative to the guidewire, including the substep of, advancing the first device to place the member into contact with the engagement structure to simultaneously insert the first and second devices.

* * * * *